US005254763A

United States Patent [19]

Gill et al.

[11] Patent Number: 5,254,763

[45] Date of Patent: Oct. 19, 1993

[54] CATALYST AND PROCESS FOR THE SELECTIVE HYDROGENATION OF BENZENE

[76] Inventors: Udai S. Gill, 146-A Craig Henry Dr., Nepean, Ontario K2G 4M6; Craig W. Fairbridge, RR #2, 3563 Diamondview Rd., Kinburn, Ontario, both of Canada; Brian A. Farnand, 18 Norwich Way, Nepean, Ontario, Canada, K2G 5R3

[21] Appl. No.: 801,395

[22] Filed: Dec. 2, 1991

[51] Int. Cl.⁵ .................................................. C07C 5/10

[52] U.S. Cl. .................................... 585/269; 585/266; 585/841; 585/850; 208/143; 208/144; 208/264

[58] Field of Search ............... 585/266, 269, 841, 850; 208/143, 144, 264

[56] References Cited

U.S. PATENT DOCUMENTS

| | | | |
|---|---|---|---|
| 3,113,986 | 12/1963 | Breslow et al. | 585/266 |
| 3,912,787 | 10/1975 | Nowack et al. | 585/269 |
| 4,197,415 | 4/1980 | Hideyuki et al. | 585/269 |
| 4,645,849 | 2/1987 | Lewis | 585/266 |
| 4,678,861 | 7/1987 | Mitsui et al. | 585/266 |
| 4,783,565 | 11/1988 | Naruse et al. | 585/266 |

FOREIGN PATENT DOCUMENTS 764502 8/1987 Canada .

*Primary Examiner*—Patrick P. Garvin
*Assistant Examiner*—E. D. Irzinski
*Attorney, Agent, or Firm*—Marcus & Associates

[57] ABSTRACT

A novel process is provided for the selective hydrogenation of benzene in a solution of gasoline and other aromatic organic compounds. The process includes the steps of carrying out the catalytic hydrogenation in a hydrogenation zone at a temperature of about 45° to about 250° C. at a pressure of about 200 psi to about 500 psi in a biphasic system of aqueous and organic liquids the hydrogenation catalyst being water-soluble. The organic liquid is removed from the hydrogenation zone. At least a catalytic amount of the catalyst is retained in the hydrogenation zone. The catalyst above described is also a facet of this invention.

4 Claims, No Drawings

CATALYST AND PROCESS FOR THE SELECTIVE HYDROGENATION OF BENZENE

BACKGROUND OF THE INVENTION (i) Field of the Invention

This invention relates to a process for selectively removing benzene from gasoline.

(ii) Description of the Prior Art

At the present time, there is environmental pressure to remove benzene, a suspected carcinogen, from gasoline. Technologies, e.g., liquid-liquid extraction or conventional hydrogenation, are presently available. However, the former may be too expensive for low quantities of benzene, and the latter may eliminate all the aromatic components, with significant loss of octane number.

In the patent literature, U.S. Pat. No. 3,767,720 describes the hydrogenation of a pure stream of liquid aromatic in the presence of an aqueous stream of reduced Group VIII cations, including ruthenium. Such process is carried out under the condition of high pH and in the presence of a reducing agent in the aqueous phase to convert the Group VIII cations to neutral species. The source of the Group VIII cations is inorganic salts. This provided a process for producing cyclohexane from benzene using a catalyst comprising a reduced cation of a group VIII element, i.e. in an aqueous solution of, e.g. $Zn^{++}$, $Cr^{++}$, $Hg^{+}$, $Hg^{++}$, $Ni^{++}$, $Mo^{++}$, $Fe^{++}$, $Fe^{+++}$, $Co^{++}$, or $Cu^{+}$.

U.S. Pat. No. 3,274,272 patented Sep. 20, 1966 by M. Amagasa et al, describes unusual liquid ammonia complexes with pure aromatic components with thermal decomposition of the ammonia, partly to saturate the aromatic component along with aqueous/metallic Group IA metals to reduce the benzene ammonia complex. It provided a process for producing cyclohexane from benzene using an alkali metal or alkaline earth metal dissolved in liquid ammonia in the presence of a decomposing agent.

U.S. Pat. No. 4,271,323 patented Jun. 2, 1981 by Durand et al, indicates that some homogenous catalysts can be used for hydrogenation of benzene as well as other components. It provided a process for hydrogenating benzene in the liquid phase in the presence of a particularly reacted soluble catalyst.

SUMMARY OF THE INVENTION (i) Aims of the Invention

The prior art is thus deficient in any teaching of selectively removing benzene from gasoline.

Accordingly, it is an object of this invention to provide a process for selectively hydrogenating benzene to an almost 100% amount in a mixture of gasoline and other aromatic compounds.

Another object of this invention is to provide a catalyst composition for the selective hydrogenation of benzene in a mixture of gasoline and other aromatic organic compounds.

The present invention features a low cost of operation, selective benzene hydrogenation, and no significant loss of octane number.

The invention utilizes a water soluble catalyst for the selective hydrogenation of benzene in a biphasic gasoline/aqueous reactor, followed by removal of the gasoline phase and reaction product, cyclohexane which is insoluble in water, thus returning the hydrocarbons to the gasoline phase.

(ii) Statement of Invention

Of the components found in gasoline, only the aromatic have significant water solubility. Further, benzene is approximately 3.5 times more soluble than toluene, which is approximately 2.5 times more soluble than the xylenes. It is thought that this water solubility can be exploited to perform the selective hydrogenation of benzene to cyclohexane without affecting toluene or xylenes.

By this invention then, a process is provided for the selective hydrogenation of benzene in an organic solution of other organic hydrocarbon compounds comprising: admixing the solution with water; adding a water-soluble organo-metallic hydrogenation catalyst; carrying out a catalytic hydrogenation in a hydrogenation zone at a temperature of about 45° to about 250° C. at a pressure of about 200 psi to about 500 psi in a biphasic system of the water and the organic solution, whereby the benzene is selectively solubilized in the water and thus is selectively hydrogenated in the presence of the water soluble organo-metallic catalyst; and recovering the organic solution from the hydrogenation zone.

(iii) Other Features of the Invention

In the process of this invention, the hydrogenation catalyst is an organo-metallic catalyst, e.g. wherein the metallic portion of the organic-metallic hydrogenation catalyst is a Group VIII metal or complex with carbon monoxide, phosphines, halides acetates, or water. Preferably, the organo-metallic catalyst is a bisbenzene ruthenium(II) chloride.

In the selective hydrogenation catalyst, the metallic portion of the organic-metallic hydrogenation catalyst is a Group VIII metal e.g., in the form of a halide, preferably a Ru(II)/chloride dimer. There is a practical relationship between the hydrogenation temperature and pressure.

The present invention uses an organic source of ruthenium in an organo-metallic form that is soluble in water and only very sparingly soluble in the organic phase.

The present invention is proposed for the selective hydrogenation of benzene only; other aromatic will not be hydrogenated in significant amounts.

There are thus two major advantages to the present invention. The first is the unique hydrogenation catalyst. The second feature is the selective hydrogenation of benzene in competition with other aromatic, organic compounds, including toluene. Since benzene has been identified as undesirable in gasoline for health reasons, it is commercially very attractive to remove the approximate 3% benzene from gasoline without affecting the benign high performance aromatic organic compounds.

In addition, a third advantageous feature of this invention is that there is no loss of catalyst since the catalyst is recycled in the aqueous phase.

DESCRIPTION OF THE PREFERRED EMBODIMENTS

The following are Examples of the process of this invention.

EXAMPLE 1

| Feed | |
|---|---|
| Water | 4.0 g |
| Toluene (with low quantities of benzene and xylenes) | 20.9 g |
| Sodium Acetate | 150 mg |
| bisbenzene ruthenium(II) chloride | 50 mg |

These were placed in a glass-lined stirred autoclave at 70° C., 460 psi of hydrogen gas, at 180 rpm for 3 days.

As observed by capillary gas chromatography, substantially all of the benzene was hydrogenated to cyclohexane and only 12% of the toluene was hydrogenated to methylcyclohexane.

To demonstrate the resistance of the catalyst to diffuse to the hydrocarbon phase from the aqueous phase, i.e. the solubility of the catalyst in water, a sample of the toluene rich phase was analyzed for its ruthenium content by Inductively Coupled Plasma Mass Spectrometry (ICPMS). It was found to contain 0.48 mg/L of ruthenium, which represents 0.037% of the ruthenium used as catalyst. This is an indication that the catalyst will not be extracted from the reactor in significant amounts.

EXAMPLE 2

Known amounts of benzene and toluene are mixed with water containing the same catalyst as described above. The mixing continued for approximately 24 hours at 70° C. and 460 psi of hydrogen.

The products were formed as follows:

| Benzene | Toluene | Xylenes | Water | Benzene Ru(II) Chloride | Sodium acetate | Benzene conversion | Toluene conversion | Xylenes conversion | Ru in organic phase |
|---|---|---|---|---|---|---|---|---|---|
| 5.205 g | 16.281 g | 0.199 g | 2.075 g | 25 mg | 100 mg | 47.9% | 16.8% | none | 0.021 mg/L |
| 3.477 g | 18.418 g | 0.256 g | 3.768 g | 30 mg | 234 mg | 37.5% | 24.0% | none | 0.076 mg/L |

EXAMPLE 3

A sample of commercial naphtha was reacted over an aqueous solution of bisbenzene ruthenium(II) chloride in an autoclave at 45° C. and 462 psig of hydrogen gas for 4 days. The product analysis showed a 47% conversion of benzene to cyclohexane. The toluene was unaffected, as were the xylenes. The ruthenium lost to the naphtha phase was 0.003 mg/L.

As described above, the biphasic (aqueous-organic) aqueous catalyst system has a great selectivity for hydrogenating benzene.

This invention can be used as a flexible, low-capital-cost reactor for the removal of carcinogenic suspect benzene from certain gasoline pool streams for which liquid extraction and non-selective hydrogenation are unsuitable. Liquid extraction is unsuitable because of its high cost, while non-selective hydrogenation is unsuitable because of reduction of octane number. Thus, the present invention provides a water soluble reactor system selectively to remove benzene, hydrogenate, and return the cyclohexane product to the gasoline feed stream. Advantages of this process include the use of water selectively to remove benzene, and the use of aqueous soluble catalysts. In addition, the octane quality would be maintained.

It is believed that the cost of such hydrogenation treatment would be about 0.54 cents(Canadian)/liter.

Conclusion

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

We claim:

1. A process for the selective hydrogenation of benzene in an organic solution of other organic hydrocarbon compounds comprising: admixing said solution with water; adding a water-soluble organo-metallic hydrogenation catalyst; carrying out a catalytic hydrogenation in a hydrogenation zone at a temperature of about 45° to about 250° C. at a pressure of about 200 psi to about 500 psi in a biphasic system of said water and said organic solution, whereby said benzene is selectively solubilized in said water and thus is selectively hydrogenated in the presence of said water soluble organo-metallic catalyst and recovering said organic solution from said hydrogenation zone.

2. The process of claim 1 wherein the metal of said hydrogenation catalyst is a Group VIII metal.

3. The process of claim 2 wherein the metallic portion of said organo-metallic hydrogenation catalyst is a Group VIII metal complex with a halogen, with carbon monoxide, with a phosphine, with an acetate or with water.

4. The process of claim 2 wherein said hydrogenation catalyst is bisbenzene ruthenium(II) chloride.

* * * * *